United States Patent
Wu et al.

(10) Patent No.: US 12,355,182 B2
(45) Date of Patent: Jul. 8, 2025

(54) CONNECTOR ASSEMBLY FOR USE IN IMPLANTABLE MEDICAL DEVICE AND MANUFACTURING METHOD THEREFOR

(71) Applicant: SCENERAY CO., LTD., Jiangsu (CN)

(72) Inventors: Guoliang Wu, Jiangsu (CN); Yuesheng Zhou, Jiangsu (CN)

(73) Assignee: SCENERAY CO., LTD, Jiangsu (CN)

( * ) Notice: Subject to any disclaimer, the term of this patent is extended or adjusted under 35 U.S.C. 154(b) by 634 days.

(21) Appl. No.: 17/767,192

(22) PCT Filed: Dec. 19, 2019

(86) PCT No.: PCT/CN2019/126673
§ 371 (c)(1),
(2) Date: Apr. 7, 2022

(87) PCT Pub. No.: WO2021/068411
PCT Pub. Date: Apr. 15, 2021

(65) Prior Publication Data
US 2022/0376433 A1 Nov. 24, 2022

(30) Foreign Application Priority Data
Oct. 8, 2019 (CN) .......................... 201910951166.4

(51) Int. Cl.
*H01R 12/71* (2011.01)
*A61N 1/375* (2006.01)
(Continued)

(52) U.S. Cl.
CPC ....... *H01R 13/5224* (2013.01); *A61N 1/3752* (2013.01); *H01R 13/111* (2013.01);
(Continued)

(58) Field of Classification Search
CPC .............. H01R 13/5224; H01R 13/111; H01R 13/5202; H01R 13/5219; H01R 43/005;
(Continued)

(56) References Cited

U.S. PATENT DOCUMENTS

| 6,895,276 B2* | 5/2005 | Kast | H01R 24/58 |
| | | | 607/37 |
| 6,934,588 B1* | 8/2005 | Brand | A61N 1/3752 |
| | | | 607/37 |

(Continued)

FOREIGN PATENT DOCUMENTS

| CN | 101018583 A | 8/2007 |
| CN | 102614584 A | 8/2012 |

(Continued)

OTHER PUBLICATIONS

Extended European Search Report in Application No. 19948467.6 dated Oct. 4, 2023, 9 pages.

(Continued)

*Primary Examiner* — Abdullah A Riyami
*Assistant Examiner* — Nelson R. Burgos-Guntin
(74) *Attorney, Agent, or Firm* — ArentFox Schiff LLP; Joseph M. Maraia; Marlo Schepper Grolnic

(57) ABSTRACT

Provided is a connector assembly for use in an implantable medical device. The connector assembly for use in an implantable medical device includes an insulating sealed housing and at least one conductive element. The sealed housing defines at least one connecting hole along an axial direction of the sealed housing, a hole wall of each of the at least one connecting hole defines at least one circumferential mounting groove, and the at least one circumferential mounting groove is arranged along an axial direction of the at least one connecting hole. The at least one conductive element is disposed in a corresponding one of the at least one (Continued)

circumferential mounting groove and is drawn out to an outside of the sealed housing through a respective electrical contact element.

26 Claims, 10 Drawing Sheets

(51) Int. Cl.
    *H01R 13/11*     (2006.01)
    *H01R 13/52*     (2006.01)
    *H01R 43/00*     (2006.01)

(52) U.S. Cl.
    CPC ..... *H01R 13/5202* (2013.01); *H01R 13/5219* (2013.01); *H01R 43/005* (2013.01)

(58) Field of Classification Search
    CPC .. H01R 2201/12; H01R 24/58; A61N 1/3752; A61N 1/362; A61N 1/37512; A61N 1/37514; A61N 1/39; A61N 1/02; A61M 5/14276; A61M 5/14244
    See application file for complete search history.

(56) References Cited

U.S. PATENT DOCUMENTS

| | | | | |
|---|---|---|---|---|
| 7,047,077 | B2* | 5/2006 | Hansen | A61N 1/3752 607/37 |
| 7,070,455 | B2* | 7/2006 | Balsells | H01R 13/33 439/668 |
| 7,195,523 | B2* | 3/2007 | Naviaux | A61N 1/3752 439/668 |
| 7,711,428 | B2* | 5/2010 | Janzig | A61N 1/3752 607/38 |
| 7,822,477 | B2* | 10/2010 | Rey | H01R 13/5224 607/37 |
| 8,091,226 | B2* | 1/2012 | Sjostedt | A61N 1/3752 29/874 |
| 8,167,660 | B2* | 5/2012 | Dilmaghanian | H01R 24/58 439/669 |
| 8,328,587 | B2* | 12/2012 | Dilmaghanian | H01R 24/58 439/827 |
| 8,666,494 | B2* | 3/2014 | Schramm | A61N 1/3752 607/37 |
| 9,168,376 | B2* | 10/2015 | Janzig | A61N 1/3752 |
| 10,091,900 | B2 | 10/2018 | Clair et al. | |
| 2003/0050549 | A1 | 3/2003 | Sochor | |
| 2004/0034393 | A1 | 2/2004 | Hansen et al. | |
| 2006/0047322 | A1 | 3/2006 | Naviaux | |
| 2008/0208277 | A1 | 8/2008 | Janzig et al. | |
| 2008/0208279 | A1 | 8/2008 | Janzig et al. | |
| 2008/0246231 | A1* | 10/2008 | Sjostedt | A61N 1/0551 29/428 |
| 2008/0255631 | A1 | 10/2008 | Sjostedt et al. | |
| 2009/0048638 | A1 | 2/2009 | Rey et al. | |
| 2015/0357749 | A1 | 12/2015 | Brunner et al. | |
| 2019/0030338 | A1 | 1/2019 | Wu et al. | |

FOREIGN PATENT DOCUMENTS

| | | |
|---|---|---|
| CN | 203103895 U | 7/2013 |
| CN | 103845802 A | 6/2014 |
| CN | 105771090 A | 7/2016 |
| CN | 105939756 A | 9/2016 |
| CN | 106232181 A | 12/2016 |
| CN | 109524863 A | 3/2019 |
| EP | 3093928 A1 | 11/2016 |

OTHER PUBLICATIONS

International Search Report from related PCT Application No. PCT/CN2019/126673, issued Apr. 2, 2020.

Office Action in related CN Application No. 201910951166.4 dated Oct. 28, 2022 (with English Translation) 18 pages.

Office Action dated Sep. 15, 2022, for related Indian Application No. 202227026171 (6 pages).

* cited by examiner

CONNECTOR ASSEMBLY FOR USE IN IMPLANTABLE MEDICAL DEVICE AND MANUFACTURING METHOD THEREFOR

CROSS-REFERENCE TO RELATED APPLICATIONS

This is a national stage application filed under 37 U.S.C. 371 based on International Patent Application No. PCT/CN2019/126673, filed Dec. 19, 2019, which claims priority to Chinese Patent Application No. 201910951166.4 filed Oct. 8, 2019, the disclosures of which are incorporated herein by reference in their entireties.

TECHNICAL FIELD

The present disclosure relates to a connector assembly for use in an implantable medical device and a manufacturing method therefor.

BACKGROUND

An implantable medical device is widely used in the diagnosis, monitoring and treatment of diseases, such as a cardiac pacemaker, a brain pacemaker, a defibrillator, a pulse generator, and a drug pump. Since a special use environment of the implantable medical device, electronic circuits and battery components of the implantable medical device are generally required to be arranged in a sealed housing. During use, the electronic circuits and battery elements arranged in the sealed housing are electrically connected to sensors and electrodes outside the sealed housing, so as to monitor specific parts of the body or provide electrical/optical stimulation. A pulse generator is used as an example. The pulse generator arranged in the sealed housing is connected to the electrode through an extended wire so that the pulse generated by the pulse generator is transmitted to the electrode arranged at a specific position, thereby performing electrical stimulation at the position.

In practice, the electrical connection between the preceding sensors or electrodes and the electronic circuits and battery elements arranged in the sealed housing is generally achieved through a connector assembly or a connection header assembly. Specifically, the connector assembly includes a conductive element and an electrical contact element that is in electrical contact with the conductive element, where the electrical contact element is electrically connected to the electronic circuits and battery elements arranged in the sealed housing, and the conductive element is electrically connected to the sensors or electrodes through the wire. During use of the preceding implantable medical device, the connector assembly must maintain a good electrical connection between the sensors or electrodes and the electronic circuits and battery elements in the sealed housing.

However, as shown in FIG. 1, the existing connector assembly or connection header assembly is generally formed as follows: multiple conductive springs 128, multiple contact rings 126 and multiple water seals 124 are nested, and then the nested and stacked conductive springs 128, contact rings 126 and water seals 124 are further encapsulated in a housing. In a process of nesting and stacking the multiple conductive springs 128, the multiple contact rings 126 and multiple water seals 124, each element is nested and fitted with each other one by one, which poses high requirements for the assembly process and precision, thereby making the whole assembly process not only cumbersome but also time-consuming. Moreover, due to a relatively large positioning error of the conductive element, poor sealing is possibly caused, thereby affecting a normal operation of the implantable medical device.

SUMMARY

The present disclosure provides a connector assembly that is easy to manufacture and can effectively avoid poor sealing.

In a first aspect of the present disclosure, a connector assembly for use in an implantable medical device is provided. The connector assembly includes an insulating sealed housing and at least one conductive element. The sealed housing defines at least one connecting hole along an axial direction of the sealed housing, a hole wall of each of the at least one connecting hole defines at least one circumferential mounting groove, and the at least one circumferential mounting groove is arranged along an axial direction of the at least one connecting hole. The at least one conductive element is disposed in a corresponding one of the at least one circumferential mounting groove and is drawn out to an outside of the sealed housing through a respective electrical contact element.

In some embodiments, the sealed housing includes at least a first insulating housing and a second insulating housing. The first insulating housing has a first mounting side, and the second insulating housing has a second mounting side. The second mounting side of the second insulating housing is sealingly connected to the first mounting side of the first insulating housing to form the sealed housing.

In some embodiments, the connector assembly further includes one or more sealing elements. The at least one connecting hole is defined by the first insulating housing or the second insulating housing or defined by connection of at least the first insulating housing and the second insulating housing.

In some embodiments, the connector assembly further includes at least one sealing element, where the at least one sealing element is respectively disposed in the at least one circumferential mounting groove, and the at least one sealing element and the at least one conductive element are alternately arranged.

In some embodiments, the connector assembly further includes at least one sealing element; the at least one circumferential mounting groove includes at least one first mounting groove and at least one second mounting groove, where the at least one first mounting groove and the at least one second mounting groove are alternately arranged; and the at least one conductive element is disposed in the at least one first mounting groove, and the at least one sealing element is disposed in the at least one second mounting groove.

In some embodiments, each of the at least one conductive element is an annular conductive element.

In some embodiments, the annular conductive element is an annular coil spring.

In some embodiments, the electrical contact element is a contact lead formed by extending a spring wire of the annular coil spring.

In some embodiments, the electrical contact element is a contact lead at least partially abutting against the annular coil spring.

In some embodiments, the contact lead at least partially abuts against the annular coil spring from an inside of the annular coil spring.

In some embodiments, the contact lead at least partially abuts against the annular coil spring from an outside of the annular coil spring.

In some embodiments, each of the at least one conductive element and a respective electrical contact element are configured to be a single element.

In some embodiments, the electrical contact element is a conductive layer disposed on a surface of the at least one circumferential mounting groove, and the conductive layer is drawn out through a through hole to the outside of the sealed housing.

In some embodiments, the connector assembly further includes at least one adapter piece, and the at least one adapter piece is electrically connected to the electrical contact element.

In some embodiments, the insulating sealed housing further includes a fixing through hole, where the fixing through hole is communicated with the at least one connecting hole and is used for installing a fixing element to fix a connector terminal inserted into the at least one connecting hole.

In some embodiments, the sealed housing defines two connecting holes aligned parallel to each other.

In some embodiments, the at least one conductive element disposed in the two connecting holes are disposed symmetrically with respect to axes of the two connecting holes.

In some embodiments, the electrical contact element is a sheet-like conductive element, and the first mounting side of the first insulating housing and the second mounting side of the second insulating housing are fixed and sealed directly or fixed and sealed through a seal structure.

In some embodiments, the seal structure includes a seal bump and a seal groove. The seal bump extends from an edge of one of the first mounting side and the second mounting side. The seal groove extends from an edge of another one of the first mounting side and the second mounting side. The seal bump and the seal groove mate with each other so as to form a fixed and sealed connection between the first insulating housing and the second insulating housing.

In some embodiments, the seal structure includes a seal groove, a profiled seal ring, and a fixing structure. The seal groove is disposed on surfaces of mounting sides of the first insulating housing and the second insulating housing. The profiled seal ring is disposed in the seal groove. The fixing structure is disposed on the first insulating housing and the second insulating housing, respectively.

In another aspect of the present disclosure, an implantable medical device is provided and includes the connector assembly described in any one of the above.

In some embodiments, the implantable medical device is an implantable pulse generator.

In another aspect of the present disclosure, a manufacturing method of a connector assembly for use in an implantable medical device is provided. The method includes providing an insulating sealed housing, where the sealed housing defines at least one connecting hole along an axial direction of the sealed housing, a hole wall of each of the at least one connecting hole defines at least one circumferential mounting groove, and the at least one circumferential mounting groove is arranged along an axial direction of the at least one connecting hole; and providing at least one conductive element, where the at least one conductive element is disposed in a corresponding one of the at least one circumferential mounting groove and is drawn out to an outside of the sealed housing through a respective electrical contact element.

In another aspect of the present disclosure, a manufacturing method of a connector assembly for use in an implantable medical device is provided. The method includes providing at least a first insulating housing and a second insulating housing, where the first insulating housing has a first mounting side, and the second insulating housing has a second mounting side, where at least the second mounting side of the second insulating housing is sealingly connected to the first mounting side of the first insulating housing to form a sealed housing; and the sealed housing defines at least one connecting hole along an axial direction of the sealed housing, a hole wall of each of the at least one connecting hole defines at least one circumferential mounting groove, and the at least one circumferential mounting groove is arranged along an axial direction of the at least one connecting hole; providing at least one conductive element, installing the at least one conductive element in a corresponding one of the at least one circumferential mounting groove, and connecting the at least one conductive element to one electrical contact element; and sealingly connecting the second mounting side of the second insulating housing to the first mounting side of the first insulating housing to form the sealed housing, and extending an end of the electrical contact element to an outside of the connector assembly.

The above is an overview of the present disclosure, and there may be simplifications, generalizations and omission of details, so it is to be noted to those skilled in the art that this part is merely illustrative and not intended to limit the scope of the present disclosure in any way. This summary section is not intended to identify key features or essential features of the claimed subject matter, nor is this summary section intended to be used as an aid in determining the scope of the claimed subject matter.

BRIEF DESCRIPTION OF DRAWINGS

The above and other features of the present disclosure are more completely and clearly understood from the following description and appended claims in conjunction with the drawings. It is to be understood that these drawings shows only several embodiments of the present disclosure and are therefore not to be construed as a limitation to the scope of the present disclosure. The content of the present disclosure is explained more clearly and in detail through the drawings.

DETAILED DESCRIPTION

Figure 1:
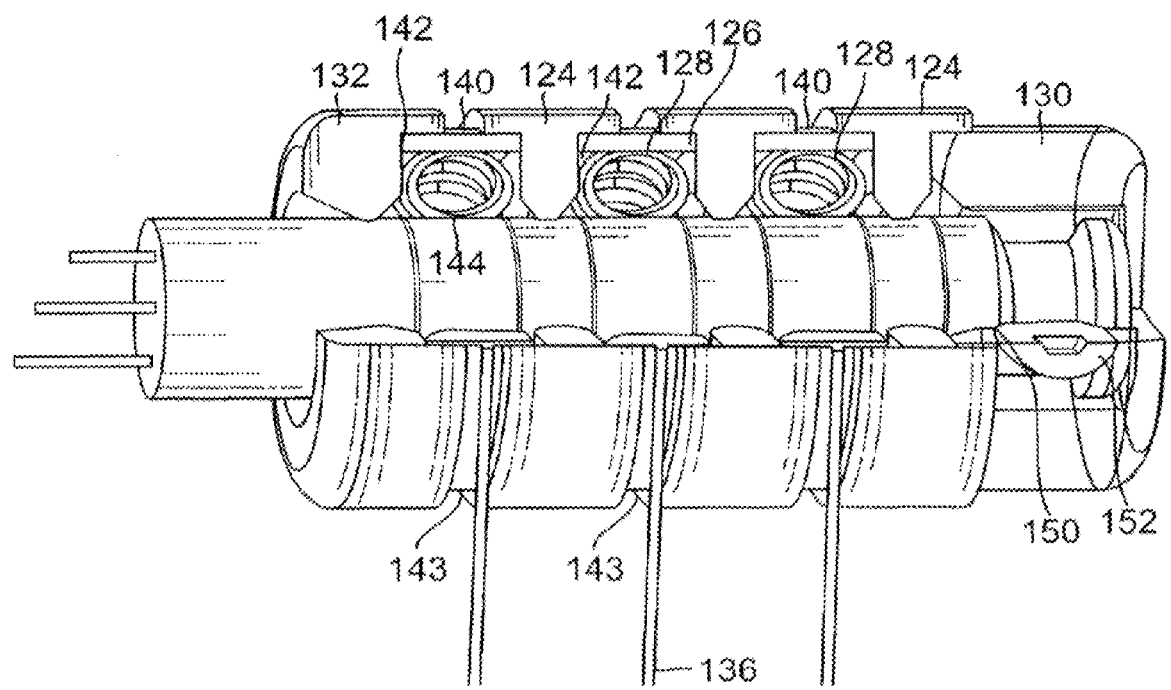
FIG. 1 is a perspective view of internal elements of a connector assembly in the existing art.

In the following detailed description, reference is made to the drawings which form a part hereof. In the drawings, similar symbols generally denote similar components, unless the context dictates otherwise. Illustrative embodiments described in the detailed description, drawings and claims are not intended to be a limitation. Other embodiments may be adopted and other variations may be made without departing from the spirit or scope of the subject matter of the present disclosure. It is to be understood that configurations, substitutions, combinations, and designs of various different compositions may be made to various aspects of the content of the present disclosure generally described in the present disclosure and illustrated in the drawings, all of which expressly constitute part of the content of the present disclosure.

Figure 2:
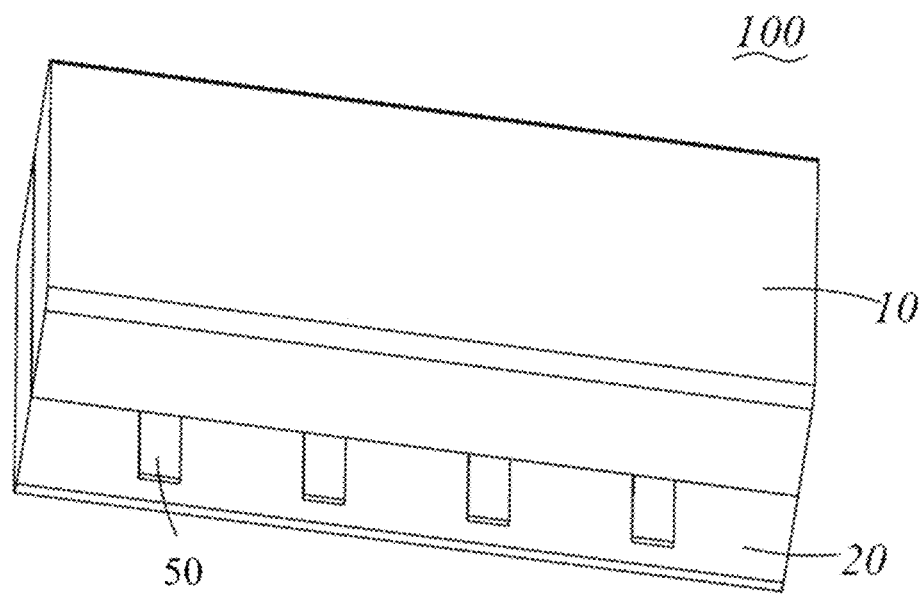
FIG. 2 is a perspective view of a connector assembly 100 according to an embodiment of the present disclosure.
Figure 3:
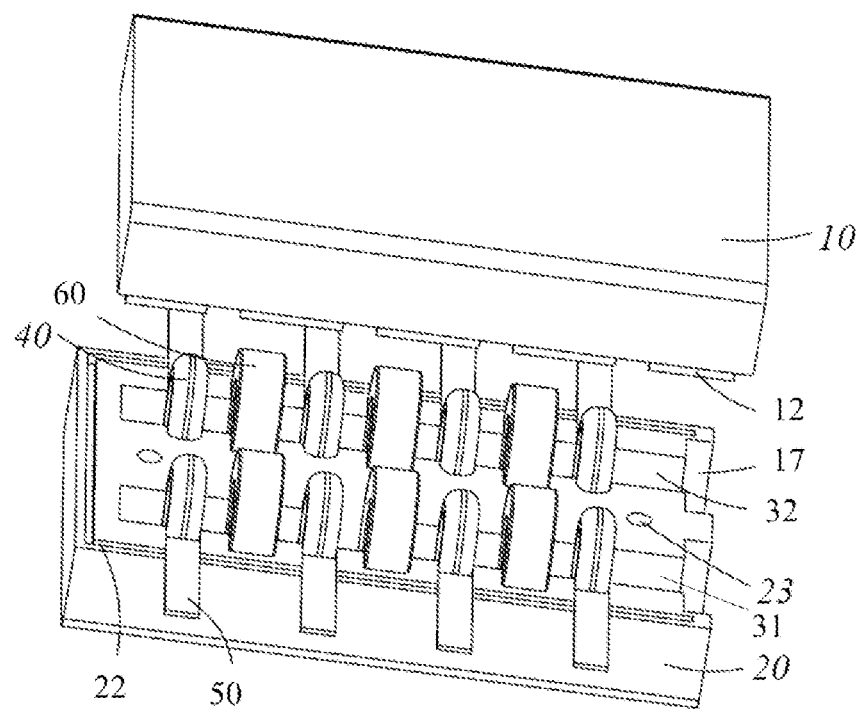
FIG. 3 is an exploded perspective view of the connector assembly 100 shown in FIG. 2.
Figure 4:
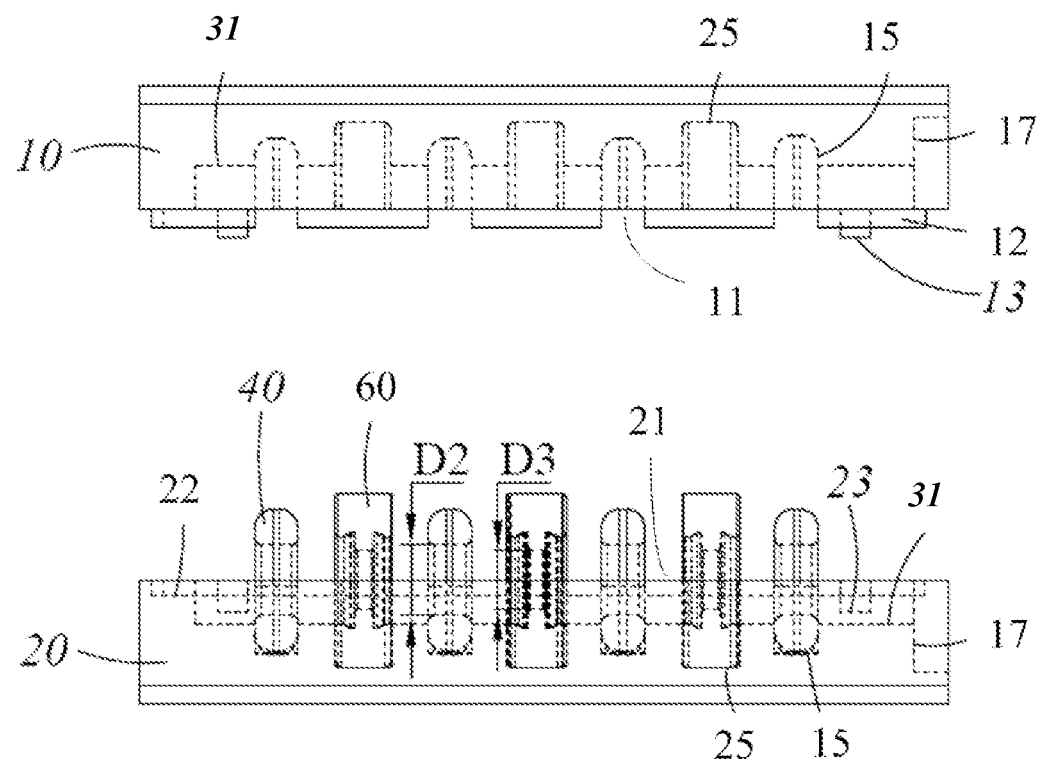
FIG. 4 is an exploded front view of the connector assembly 100 shown in FIG. 3.
Figure 5:
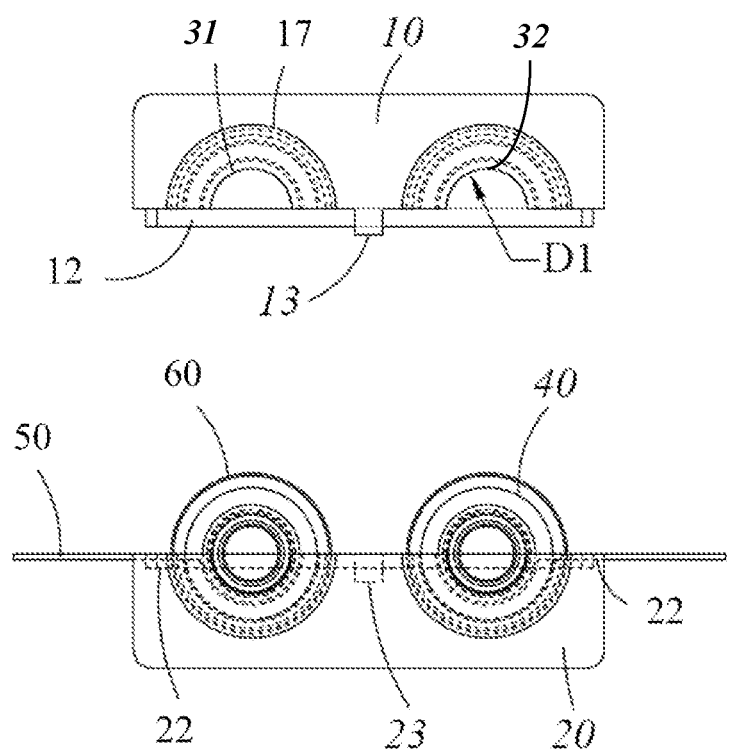
FIG. 5 is an exploded right view of the connector assembly 100 shown in FIG. 3.
Figure 6:
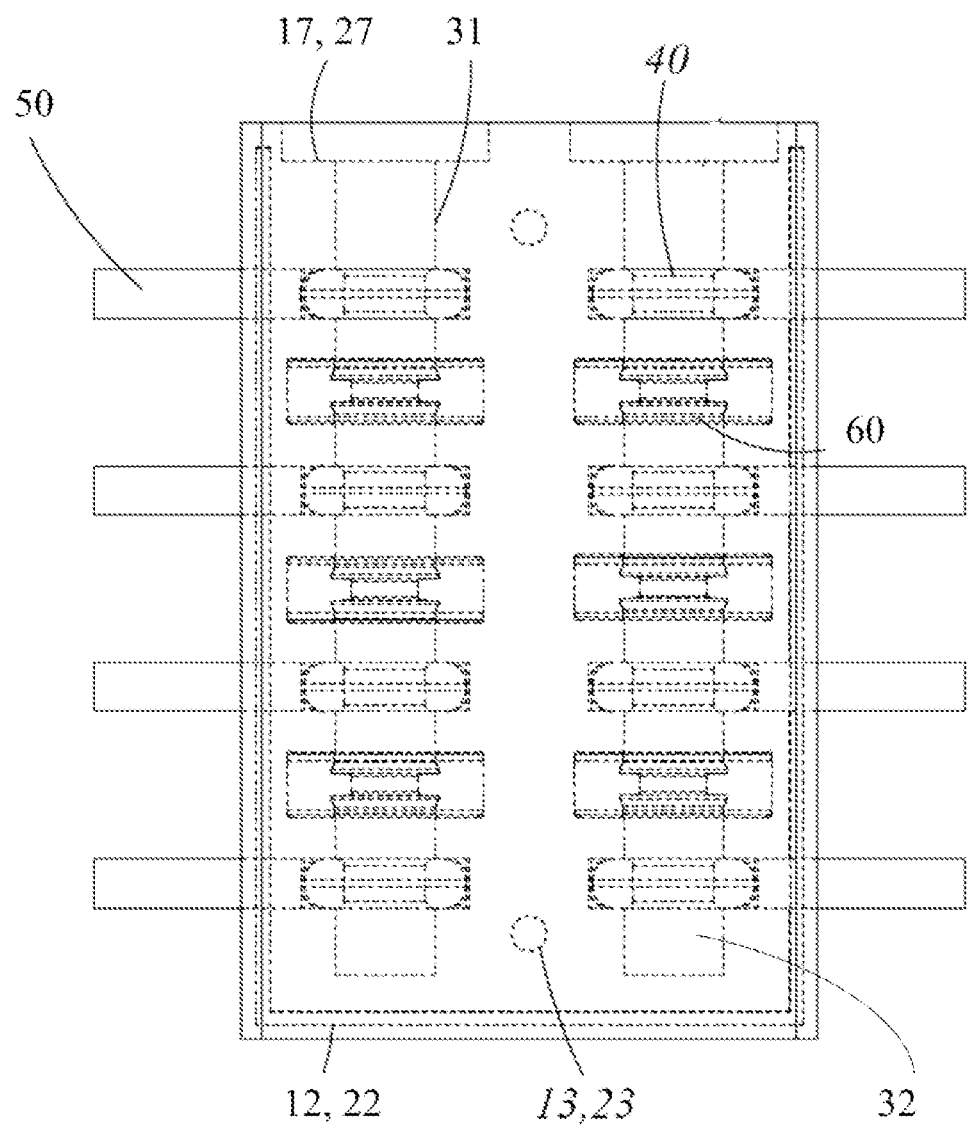
FIG. 6 is a top view of the connector assembly 100 shown in FIG. 5.

FIG. 2 is a perspective view of a connector assembly 100 according to an embodiment of the present disclosure. FIG. 3 is an exploded perspective view of the connector assembly 100 shown in FIG. 2. FIG. 4 is an exploded front view of the connector assembly 100 shown in FIG. 3. FIG. 5 is a right view of the connector assembly 100 shown in FIG. 3. FIG. 6 is a top view of the connector assembly 100 shown in FIG. 5.

Figure 12:
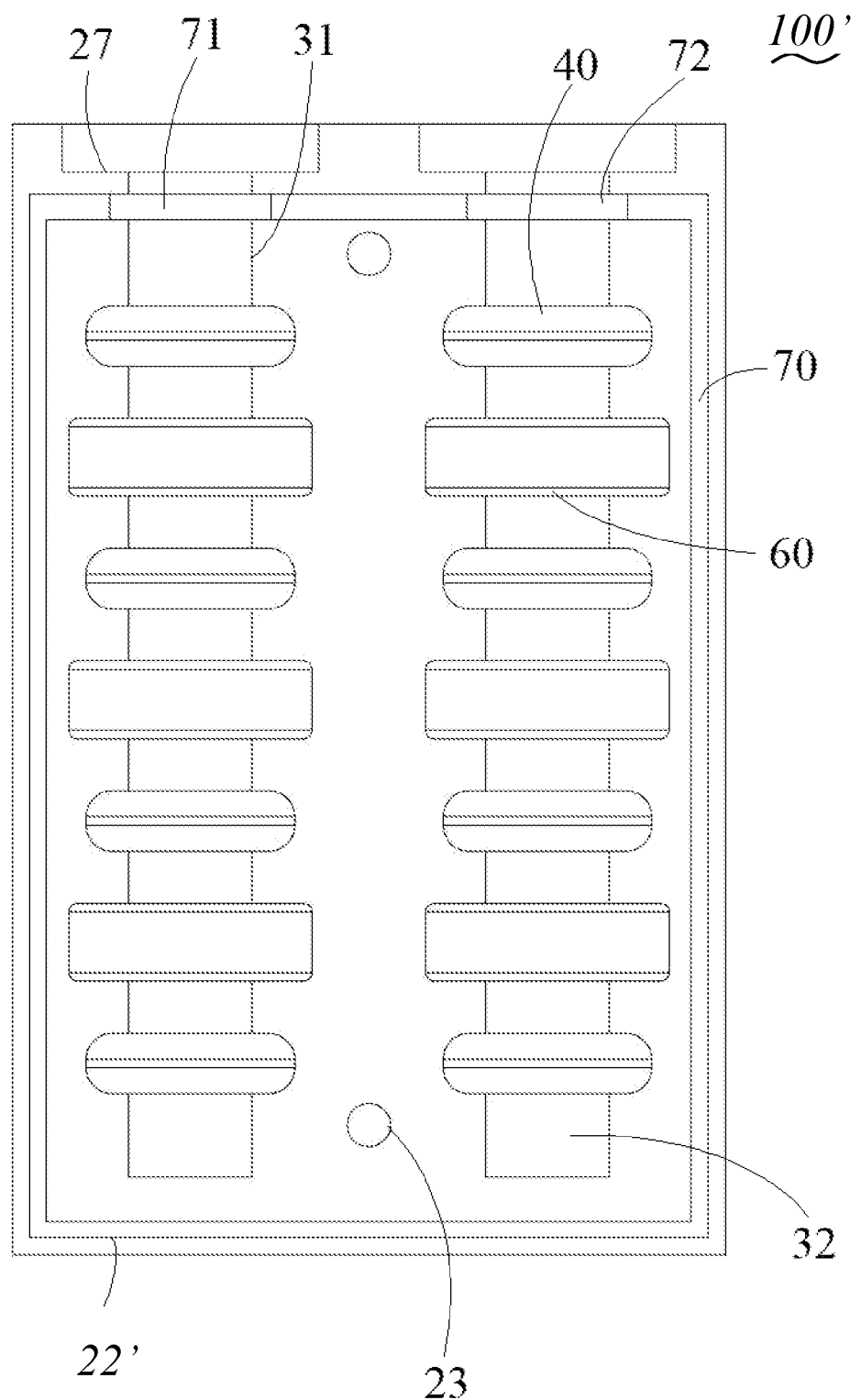
FIG. 12 is a top view of a connector assembly 100' with a first insulating housing 10 removed according to an embodiment of the present disclosure.
Figure 13:
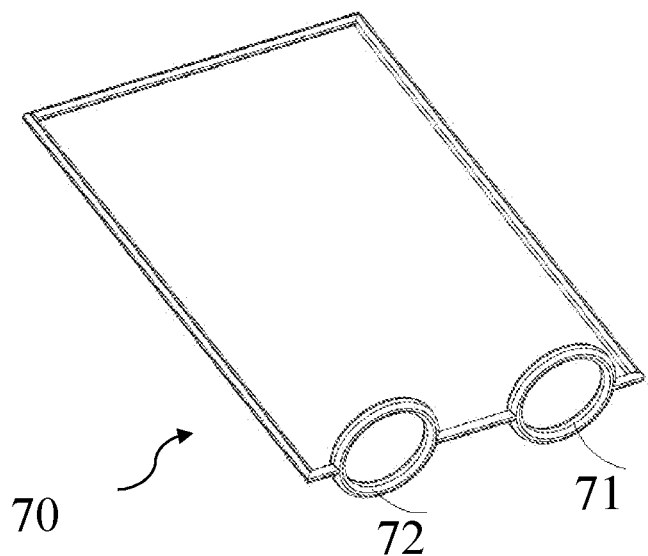
FIG. 13 is a perspective view of a profiled seal ring applied to the connector assembly 100' shown in FIG. 12.
Figure 14:
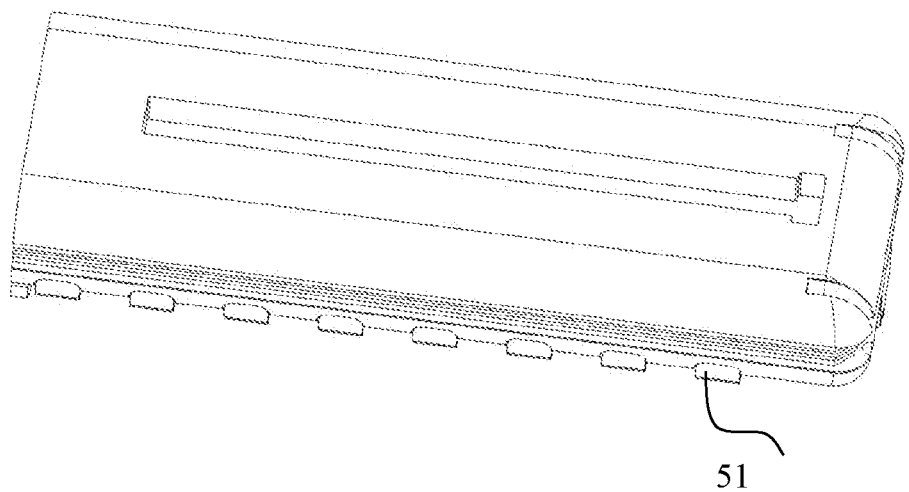
FIG. 14 is a perspective view of a connector assembly 500 according to an embodiment of the present disclosure.

As shown in FIGS. 2 to 6, the connector assembly 100 includes a first insulating housing 10 and a second insulating housing 20. In an embodiment, as shown in FIGS. 4 and 5, the first insulating housing 10 has a first mounting side 11, the second insulating housing 20 has a second mounting side 21, and the first mounting side 11 of the first insulating housing and the second mounting side 21 of the second insulating housing 20 can be sealingly connected to each other so that the first insulating housing 10 and the second insulating housing 20 are installed together, thereby forming a joint surface sealed housing. In some embodiments, the first mounting side 11 of the first insulating housing 10 abuts against the second mounting side 21 of the second insulating housing 20, and the first insulating housing 10 and the second insulating housing 20 are fixed, sealed and connected together through a seal structure. In an embodiment, as shown in FIGS. 3 to 5, a seal bump 12 extends from an edge of the first mounting side 11 of the first insulating housing 10, and a seal groove 22 extends from an edge of the second mounting side 21 of the second insulating housing 20 opposite to the first mounting side 11 of the first insulating housing 10. A position and shape of the seal groove 22 are configured to be capable of accommodating the seal bump 12 of the first insulating housing 10 so that the seal bump 12 may sink into the seal groove 22, thereby achieving a mutually fixed and sealed connection between the first insulating housing 10 and the second insulating housing 20. In some embodiments, a groove width of the seal groove 22 is equal to or slightly less than a corresponding width of the seal bump 12 so that an interference connection between the seal bump 12 and the seal groove 22 is formed, thereby achieving a better sealing effect. In some embodiments, the seal bump 12 may be made of an elastic material, or an elastic cushion may be disposed in the seal groove 22, so as to form a better sealing effect between the seal bump 12 and the seal groove 22. It is to be noted that although the seal groove 22 shown in the figures is configured to substantially surround most of the edge of the second mounting side 21 of the second insulating housing 20, in some embodiments, the seal groove 22 and the corresponding seal bump 12 may also be configured to extend around partial edges of the second insulating housing 20 and the first insulating housing 10, respectively. In some embodiments, multiple rings of seal bumps may extend along the edge of the second mounting side 21, and multiple rings of seal grooves may extend along an edge of the mounting side 22. In other embodiments, the second mounting side 21 may have both the seal groove and the seal bump, and the mounting side 22 may also have both the corresponding seal bump and the seal groove. Multi-layer sealing may better improve a sealing performance of the connection between the first insulating housing and the second insulating housing and prevent liquid from leaking into the connector assembly. In some embodiments, as shown in FIGS. 12 and 13, a seal groove 22' is disposed on a surface of the second mounting side 21 of the second insulating housing 20, and correspondingly, a seal groove (not shown) is disposed on a surface of the first mounting side 11 of the first insulating housing 10. Seal grooves of the first insulating housing 10 and the second insulating housing 20 jointly define a sealed space. A difference between the seal groove here and the seal groove 12 (22) is that this seal groove forms a closed curve on the surfaces of the first mounting side 11 of the first insulating housing 10 and the second mounting side 21 of the second insulating housing 20, and a profiled seal ring 70 is provided and may be placed in the sealed space. The profiled seal ring 70 has annular portions 71 and 72 greater than orifices 17 and 27 near the orifices 17 and 27 of connecting holes 31 and 32 defined by the first insulating housing 10 and the second insulating housing 20. The first insulating housing 10 and the second insulating housing 20 are provided with fixing structures that mate with each other, so as to fix the profiled seal ring 70 to the sealed space jointly defined by the seal grooves of the first insulating housing 10 and the second insulating housing 20. In addition, an outer diameter of the profiled seal ring is greater than or equal to an inner diameter of the sealed space, so as to form an interference fit, thereby having an excellent sealing effect.

Other forms of seal structures may be adopted to form the sealing between the first insulating housing 10 and the second insulating housing 20. In some embodiments, after the first mounting side 11 of the first insulating housing 10 abuts against and is aligned with the second mounting side 21 of the second insulating housing 20, a sealing strip is wrapped around a seam between the first insulating housing 10 and the second insulating housing 20, so as to achieve sealing. In other embodiments, the seam between the first insulating housing 10 and the second insulating housing 20 may be directly sealed without using a seal structure. For example, after the first mounting side 11 of the first insulating housing 10 abuts against and is aligned with the second mounting side 21 of the second insulating housing 20, ultrasonic welding or adhesive bonding is performed along the seam between the first insulating housing 10 and the second insulating housing 20 so that materials of the first insulating housing 10 and the second insulating housing 20 are fused to each other along the seam, thereby forming the effective sealing.

In some embodiments, the first insulating housing and the second insulating housing may be made of transparent materials, such as polycarbonate or polyetheretherketone. The housing structure made of transparent materials is easy to observe the inside of the connector during installation and use.

As shown in FIGS. 3 to 5, a pair of protruding positioning posts 13 may also be disposed on the first mounting side 11 of the first insulating housing 10, and a pair of positioning post holes 23 substantially mating with the positioning posts 13 in shape may be disposed on the second mounting side 21 of the second insulating housing 20. During a process of connecting the first insulating housing 10 to the second insulating housing 20, the positioning posts 13 are inserted into corresponding positioning post holes 23 and move along an axial direction of the positioning post holes 23, thereby achieving the precise alignment between the first insulating housing 10 and the second insulating housing 20.

Referring to FIGS. 4 to 6, after the first mounting side 11 of the first insulating housing 10 abuts against and is aligned with the second mounting side 21 of the second insulating housing 20, the first insulating housing 10 is connected to the second insulating housing 20 so as to define a pair of connecting holes 31 and 32, the connecting holes 31 and 32 have the orifices 17 and 27, and connector terminals (not shown in the figure) of externally extending wires connected to sensors or electrodes may be inserted into the connecting holes 31 and 32 through the orifices 17 and 27. When inserted into the connecting holes 31 and 32, the connector terminals can be in electrical contact with conductive elements (the specific structure and arrangement are described in detail below) of the connector assembly 100 disposed in the connecting holes 31 and 32.

In some embodiments, the connecting hole may be defined only in the second insulating housing 20, and the first insulating housing 10 does not define the connecting hole. In other words, the mounting side of the first insulating housing 10 is generally a plane. In this manner, when the first mounting side 11 of the first insulating housing 10 abuts against and is aligned with the second mounting side 21 of the second insulating housing 20, the first insulating housing 10 encloses a corresponding connecting hole part on the second insulating housing 20.

In some embodiments, the connection hole may be defined only in the first insulating housing 10.

Figure 9:
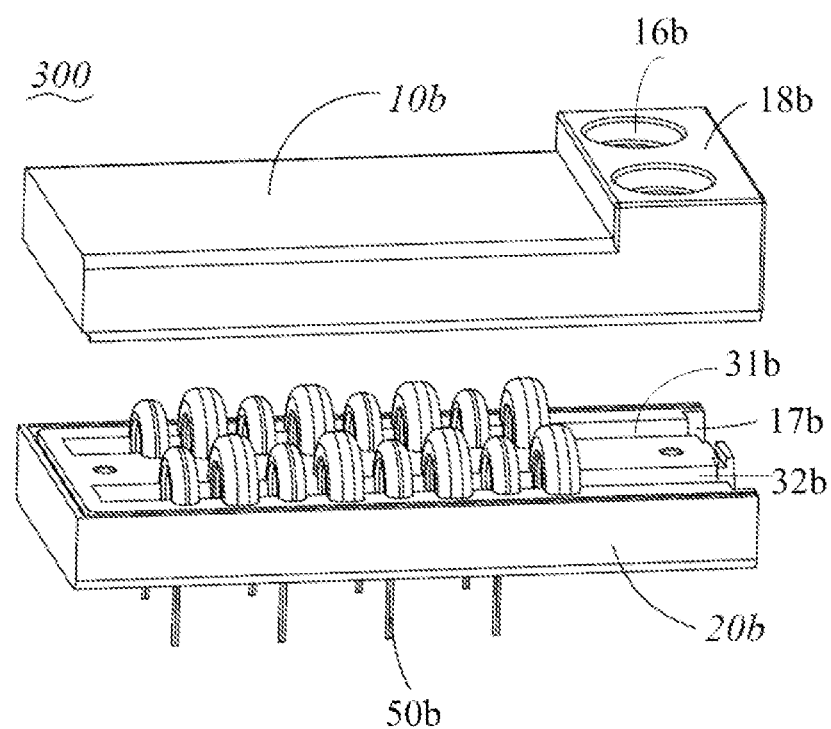
FIG. 9 is an exploded perspective view of a connector assembly 300 according to an embodiment of the present disclosure.

FIG. 9 is an exploded perspective view of a connector assembly 300 according to an embodiment of the present disclosure. As shown in FIG. 9, a step 18b protrudes from one side adjacent to an orifice of a connecting hole 31b or 32b formed by a first insulating housing 10b and a second insulating housing 20b and is disposed on an opposite side wall of the mounting side of the first insulating housing 10b. On the step 18b, a pair of fixing through holes 16b are provided and communicated with the connecting holes 31b and 32b, respectively. After the connector terminals (not shown in the figure) connected to the externally extending wires are inserted into the connecting holes 31b and 32b, fasteners such as pins or screws are inserted through the fixing through holes 16b so as to better fix the connector terminals inserted into the connecting holes 31b and 32b, thereby preventing the following problem: the connector terminals loosen relative to the connector assembly and poor electrical contact is caused. Although the fixing through holes 16b shown in FIG. 9 are formed in the step 18b on the opposite side wall of the mounting side of the first insulating housing 10b, other alternative arrangements may be adopted. For example, in some embodiments, the fixing through holes 16b may be directly disposed on the opposite side wall of the mounting side of the first insulating housing 10b and adjacent to the orifices of the connecting holes. In some embodiments, the fixing through holes 16b may also be disposed on an adjacent side wall of the mounting side of the first insulating housing 10b or the second insulating housing 20b and communicated with the connecting holes 31b and 32b. In some embodiments, corresponding pin holes or screw holes may be disposed on the connector terminals connected to the externally extending wires, so as to better cooperate with the fasteners inserted into the fixing through holes 16b to form a more stable connection.

Although in the embodiment shown in FIGS. 3 and 5, the first insulating housing 10 and the second insulating housing 20 are connected to each other so as to form the sealed housing and define the two connecting holes 31 and 32, which is only an example. At least one of the first insulating housing 10 or the second insulating housing 20 may form a certain number of connecting holes so that when the first insulating housing 10 and the second insulating housing 20 are connected to each other, a certain number of connecting holes may be formed, for example, 1, 3, 4, 5, 6 or more connecting holes are formed.

Referring to FIGS. 3 to 6, the first insulating housing 10 and the second insulating housing 20 further include multiple grooves 15 and 25, respectively. When the first insulating housing 10 is aligned with and installed to the second insulating housing 20, the multiple grooves 15 and grooves 25 are respectively aligned with each other in pairs so as to form annular circumferential mounting grooves that are concave and substantially around the connecting holes 31 and 32, where the circumferential mounting grooves include a first circumferential mounting groove and a second circumferential mounting groove. In some embodiments, since groove depths of the grooves 15 and 25 are not the same, groove depths of multiple circumferential mounting grooves are not the same so that the multiple circumferential mounting grooves are used for installing different elements, which is described below. In some embodiments, as shown in FIG. 3, the multiple circumferential mounting grooves are arranged at intervals along an axial direction of the connecting hole 31.

As shown in FIGS. 3 to 5, the connector assembly 100 further includes multiple conductive elements 40 disposed in the circumferential mounting grooves. Referring to FIGS. 3 and 5, the conductive element 40 is an annular conductive element. In an embodiment, as shown in FIG. 4, inner surfaces of the first insulating housing 10 and the second insulating housing 20 are in direct contact with the conductive elements 40 so as to provide effective support for the conductive elements 40 and enable the conductive elements 40 to be installed on the first insulating housing 10 and the second insulating housing 20. When the connector terminal is inserted into the connecting hole and abuts against the conductive element 40, the first insulating housing 10 and the second insulating housing 20 may provide an effective supporting force to bias the conductive element 40 to an outer surface of the connector terminal, thereby achieving the stable and effective electrical contact between the conductive element 40 and the connector terminal. In some embodiments, a spacer may be disposed between the conductive element 40 and the first insulating housing 10 and the second insulating housing 20. In the case where the conductive element 40 is an annular conductive element, the spacer is a corresponding annular spacer. In some embodiments, the inner surfaces of the first insulating housing 10 and the second insulating housing 20 are not in direct contact with the conductive element 40, and a support element, such as an annular support element disposed around the conductive element 40, is disposed between the inner surfaces of the first insulating housing 10 and the second insulating housing 20 and the conductive element 40. In some embodiments, the support element has elasticity so that when the connector terminal is inserted into the connecting hole and abuts against the conductive element 40, the support element provides a sufficient supporting force to the conductive element 40, thereby ensuring the stable and effective electrical contact between the conductive element 40 and the connector terminal.

Although the conductive element 40 is shown as a circular shape, in some embodiments, the conductive element 40 may be of other shapes, such as a square, a pentagon, a hexagon, an oval, and the like. In some embodiments, the conductive element 40 may also be a segmented structure. For example, one or more segmented conductive elements may be installed in each mounting groove and substantially arranged circumferentially along the mounting groove so that when a connector plug is inserted into the connector assembly 100, the segmented conductive elements can be in contact with the connector plug from different directions of a position corresponding to the connector plug. Along with the change of the shape and arrangement of the conductive element 40, the shape of the corresponding circumferential mounting groove may also be correspondingly changed so that the conductive element 40 is positioned at an appropriate position. For example, for the segmented conductive element 40, the corresponding circumferential mounting groove does not need to be a concave annular groove along a circumferential wall of the connecting hole, but may be only a part of the annular groove. It is to be understood that individual segments of the segmented conductive element 40 need to be electrically connected, either directly or indirectly.

In some embodiments, the connector assembly 100 further includes multiple electrical contact elements, and each electrical contact element has a first end and a second end opposite to the first end, where the first end is directly electrically connected to a corresponding conductive element, and the second end is external to the connector assembly. Although the electrical contact element and the conductive element are not sleeved with, for example, a conductive ring to reduce a contact resistance between the electrical contact element and the conductive element, since the connector assembly is generally used in the implantable medical device and a diameter of the connector assembly is relatively small, the contact resistance between the electrical contact element and the conductive element that are directly electrically connected is still relatively small, thereby satisfying the requirements of a practical application. In addition, since the conductive ring does not need to be used, the installation and material costs of the connector assembly in embodiments of the present disclosure are greatly reduced. In an embodiment, as shown in FIGS. 2, 3, 5 and 6, the connector assembly 100 includes multiple electrical contact elements 50, where the electrical contact element 50 is a sheet-like conductive element, and one end of the sheet-like conductive element is connected to the annular conductive element 40. After the first insulating housing 10 is installed and connected to the second insulating housing 20, the multiple electrical contact elements are sandwiched between the mounting sides of the first insulating housing 10 and the second insulating housing 20, and the sheet-like conductive elements 50 extend to an outside of the sealed housing formed by the first insulating housing 10 and the second insulating housing 20. It is to be understood that, at a position where the sheet-like conductive element 50 overlaps with the edges of the first insulating housing 10 and the second insulating housing 20, a thickness of the seal bump between the two housings may be reduced, or a depth of the seal groove may be reduced, thereby allowing the sheet-like conductive element to extend from between the housings while maintaining the sealing performance. In some embodiments, the sheet-like conductive elements 50 may also extend out of the sealed housing formed by the first insulating housing 10 and the second insulating housing 20 from lead holes formed on an opposite or adjacent side wall of the mounting side of the first insulating housing or the second insulating housing. In some embodiments, the electrical contact elements 50 may also have other shapes or arrangements.

FIGS. 7 to 10 illustrate connector assemblies according to other embodiments of the present disclosure. The connector assemblies adopt electrical contact elements different from the electrical contact elements in the embodiments shown in FIGS. 2 to 6.

Figure 7:
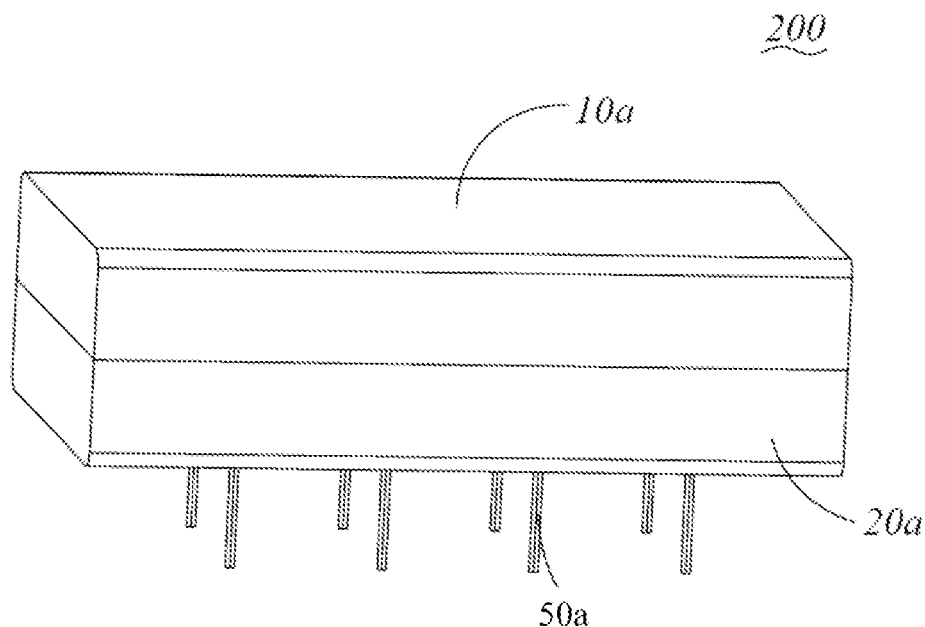
FIG. 7 is a perspective view of a connector assembly 200 according to an embodiment of the present disclosure.
Figure 8:
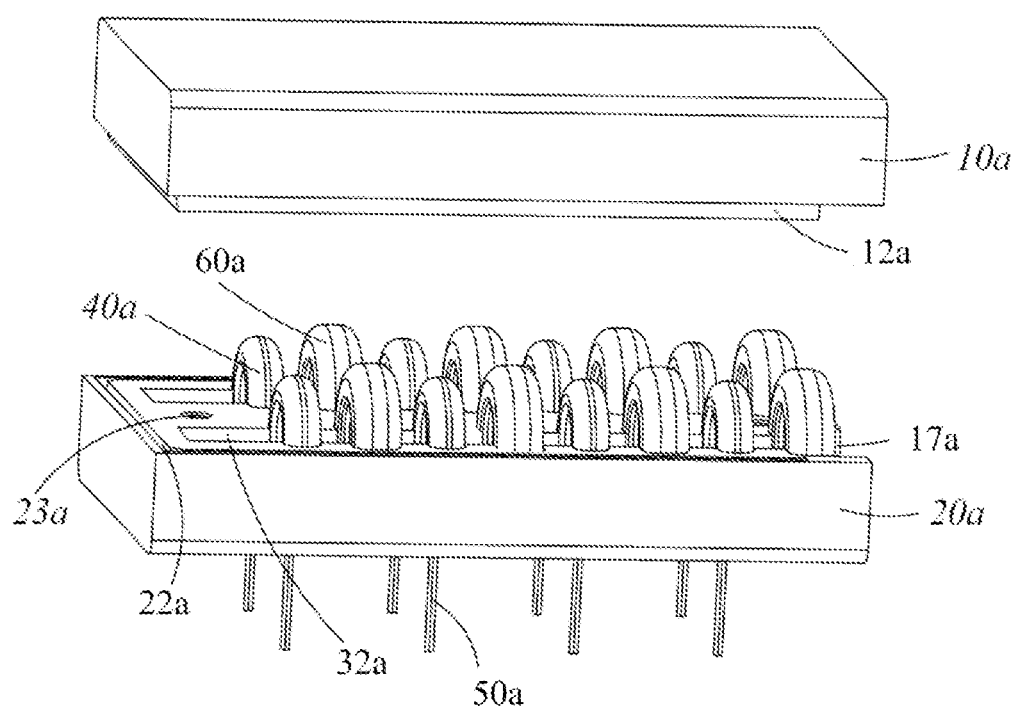
FIG. 8 is an exploded perspective view of the connector assembly 200 shown in FIG. 7.
Figure 10:
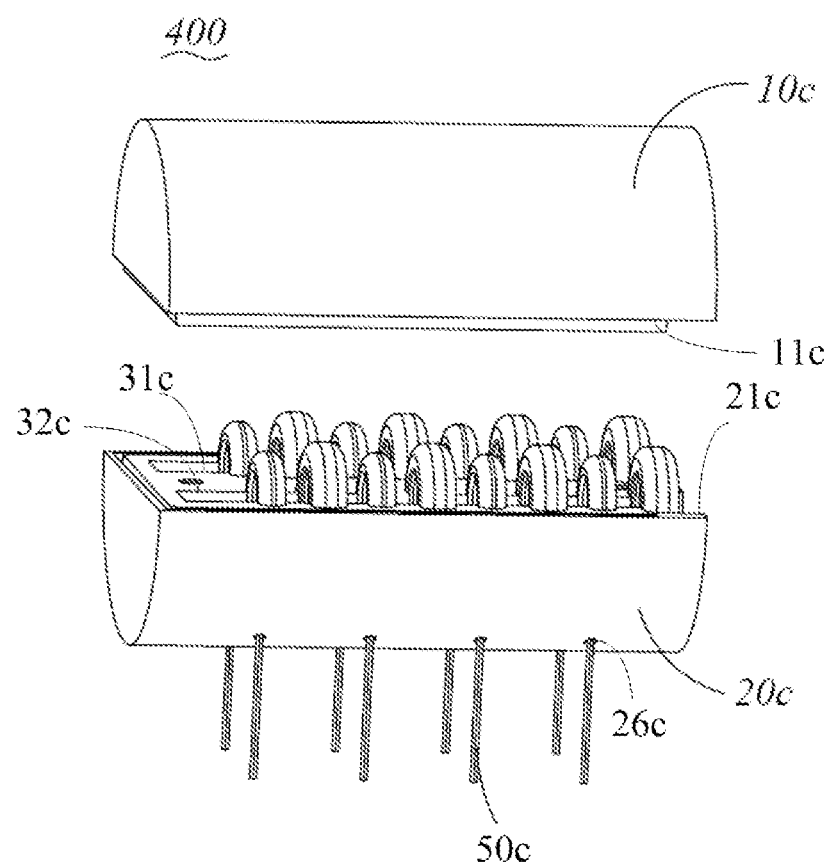
FIG. 10 is an exploded perspective view of a connector assembly 400 according to an embodiment of the present disclosure.

In an embodiment, FIG. 7 is a perspective view of a connector assembly 200 according to an embodiment of the present disclosure. FIG. 8 is an exploded perspective view of the connector assembly 200 shown in FIG. 7. FIG. 9 is an exploded perspective view of a connector assembly 300 according to an embodiment of the present disclosure. FIG. 10 is an exploded perspective view of a connector assembly 400 according to an embodiment of the present disclosure. The connector assembly 400 differs from the connector assembly 300 mainly in that external shapes are slightly different. A shape of the connector assembly 300 is substantially a cube, and a shape of the connector assembly 400 is substantially a cylinder. It is to be understood that, according to different embodiments, the external shape of the connector assembly may be adjusted adaptively.

As shown in FIGS. 7 to 10, the electrical contact elements 50a to 50c are linear or columnar, respectively. In an embodiment, as shown in FIG. 10, multiple lead holes 26c are disposed on a side wall opposite to a second mounting side 21c on a second insulating housing 20c of the connector assembly 400, and an electrical contact element 50c extends through the lead hole 26c from a connecting hole 31c or 32c to an outside of the connector assembly 400. As shown in FIG. 10, each lead hole 26c corresponds to one electrical contact element 50c. In some embodiments, each lead hole may also correspond to multiple electrical contact elements (not shown in the figure), that is, the multiple electrical contact elements extend to the outside of the connector assembly through a single lead hole.

In some embodiments, the multiple lead holes 26c may be disposed on a side surface opposite to a first mounting side 11c of a first insulating housing 10c. In some embodiments, the multiple lead holes may be disposed on side walls adjacent to, but not opposite to the mounting side of the first insulating housing 10c or the second insulating housing 20c. The number of lead holes is generally set to correspond to the number of electrical contact elements 50c of the connector assembly. In some embodiments, only one lead hole 26c is disposed on a side wall of the first insulating housing 10c or the second insulating housing 20c.

In some embodiments, the electrical contact element is a conductive layer (not shown) on an inner surface of the circumferential mounting groove and in the lead hole. In an embodiment, the conductive layer is disposed on a surface of the circumferential mounting groove for installing the conductive element 40 and in the lead hole communicated with the circumferential mounting groove. Conductive layers on surfaces of adjacent circumferential mounting grooves are separated. FIGS. 3 and 4 are used as an example. The conductive layers replace the electrical contact elements 50 and are only disposed on surfaces of the grooves 15 for installing the conductive elements 40. For the lead holes, reference may be made to FIGS. 7 to 10, the lead holes are communicated with the circumferential mounting grooves, and the conductive layers may fill the lead holes so as to form lead structures similar to leads 50a to 50c. An electrical signal is conducted to the conductive layer on the surface of the groove 15 through the conductive layer in the lead hole, then, through the conductive element 40, to the connector terminal of the externally extending wire in contact with the conductive element 40, and finally to the electrode through the externally extending wire, thereby achieving electrical stimulation at a corresponding position.

With continued reference to FIGS. 2 to 6, the conductive element 40 and the electrical contact element 50 are electrically connected to each other. In some embodiments, the conductive element 40 and the electrical contact element 50 are fixedly connected to each other in a non-detachable manner such as welding, bonding or cold pressing. In some embodiments, the conductive element 40 and the electrical contact element 50 may be detachably connected to each other by inlay, snap fit or the like.

In embodiments such as those shown in FIGS. 7 to 10, the conductive element 40 and the electrical contact elements 50a to 50c may be integrally formed, that is, the conductive element 40 and the electrical contact elements 50a to 50c are configured to be a single element. For example, the conductive element may be an annular coil spring, and the electrical contact element of the conductive element is a contact lead directly formed by extending a spring wire of the conductive element which is the annular coil spring. The conductive element configured in this manner is adopted so that the production and assembly efficiency of the connector assembly can be improved, and the occurrence of poor contact can be effectively avoided. In some embodiments, after electrical contact elements or contact leads extend from the sealed housing formed by the first insulating housing and the second insulating housing of the connector assembly, the electrical contact elements or the contact leads are electrically connected to electronic circuits and battery elements disposed in the sealed housing of the implantable medical device.

Figure 11:
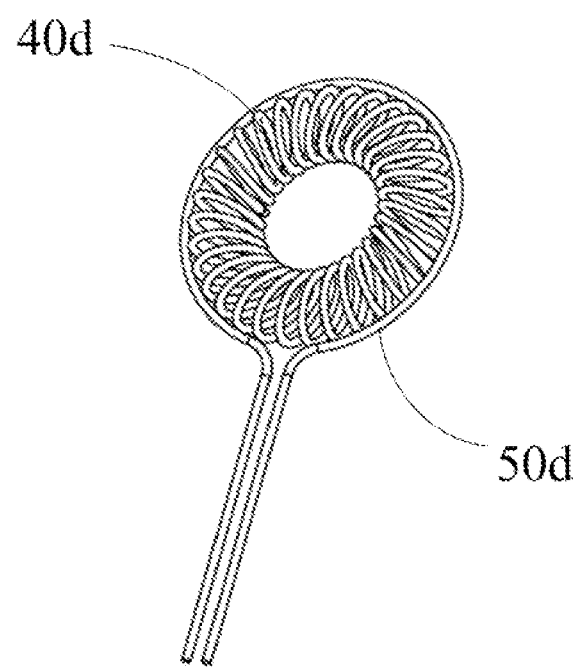
FIG. 11 shows a conductive element 40d and an electrical contact element 50d of a connector assembly according to an embodiment of the present disclosure.

In some embodiments, the conductive element is a conductive annular coil spring, and the electrical contact element is a contact lead at least partially abutting against the annular coil spring. In some embodiments, the electrical contact element is a contact lead that at least partially abuts against the annular coil spring along an inside of the annular coil spring. In other embodiments, the electrical contact element is a contact lead that at least partially abuts against the annular coil spring along a circumference of the annular coil spring. FIG. 11 shows a conductive element 40d and an electrical contact element 50d of a connector assembly according to an embodiment of the present disclosure. As shown in FIG. 11, the illustrated conductive element 40d is an annular coil spring, and the electrical contact element 50d is a contact lead that abuts against the annular coil spring substantially around the circumference of the entire annular coil spring. In some embodiments, the electrical contact element 50d may be configured to apply pressure to the conductive element 40d along the circumference of the conductive element 40d in a resting state, thereby forming the good and reliable electrical contact between the conductive element 40d and the electrical contact element 50d.

Referring to FIGS. 7 to 11 and 14, the connector assembly 500 according to an embodiment of the present disclosure further includes an adapter piece 51. The electrical contact elements 50a to 50d in different embodiments are electrically connected to the adapter piece 51, and moreover, the adapter sheet 51 is electrically connected to an applied medical device.

With continued reference to FIGS. 3 to 5, the connector assembly 100 further includes one or more sealing elements 60. As shown in the figure, similar to the conductive elements 40, one or more sealing elements 60 are also arranged in the circumferential mounting grooves, respectively. Generally, only at least one conductive element or at least one sealing element is installed in a same mounting groove, but in some embodiments, the conductive element and the sealing element may also be installed in the same circumferential mounting groove. For example, one conductive element and one sealing element are clamped together in the circumferential mounting groove. In some embodiments, the circumferential mounting groove includes a first circumferential mounting groove formed by the groove 15 and a second circumferential mounting groove formed by the groove 25, at least one conductive element and at least one sealing element are placed in the first circumferential mounting groove and the second circumferential mounting groove, respectively, and a sealing element 60 is arranged between two adjacent conductive elements 40, so as to separate the two adjacent conductive elements 40 from each other.

In some embodiments, multiple conductive elements 40 and multiple sealing elements 60 are alternately arranged along the axial direction of the connecting hole in which the multiple conductive elements 40 and the multiple sealing elements 60 are located. As shown in FIGS. 3 to 5, multiple conductive elements 40 and multiple sealing elements 60 alternately arranged in the connecting hole 31 along the axial direction of the connecting hole are symmetrical to the conductive elements 40 and the sealing elements 60 alternately arranged in the connecting hole 32. Although in the embodiment shown in the figure, the conductive elements 40 adjacent to each other are spaced apart from the sealing elements 60 by a distance, in other embodiments, at least part of the conductive elements 40 may also abut against the sealing elements 60 adjacent to the at least part of the conductive elements 40, which is conducive to reducing an axial length of the connector.

As shown in FIG. 5, both the conductive element 40 and the sealing element 60 have central holes or openings, and respective central holes or openings are substantially aligned with the connecting hole 31 or 32 where the conductive element 40 and the sealing element 60 are located so that the conductive element 40 and the sealing element 60 and the connecting hole 31 or 32 where the conductive element 40 and the sealing element 60 are located together form holes into which the connector terminals of the externally extending wires are inserted. As shown in FIGS. 4 and 5, an inner diameter D1 of the connecting hole 31 or 32 is greater than an inner diameter D2 of a central hole of the conductive element 40, and the inner diameter D2 of the central hole of the conductive element 40 is greater than an inner diameter D3 of a central hole of the sealing element 60. The diameters are set in this manner so that when the connector terminal is inserted into the connecting hole 31 or 32, the conductive element 40 may form a relatively tight fit with the connector terminal so as to maintain a good and durable electrical connection, and the sealing element 60 may form a tighter fit with the connector terminal, thereby achieving a better sealing effect. It should be pointed out that although central openings of the conductive element 40 and the sealing element 60 are shown as circular holes, in some embodiments, the central openings of the conductive element 40 and the sealing element 60 may also be configured to be other shapes, such as a triangle, a square, and a pentagon, that mate with an outer contour of the connector terminal.

The conductive element 40 and the electrical contact element 50 as described above may be made of conductive materials, such as metallic materials or conductive composite materials. In some embodiments, the conductive element 40 and the electrical contact element 50 may be formed of a non-metallic material whose surface is coated with a metallic material. In some embodiments, the sealing element 60 may be made of an insulating elastic material. In some embodiments, the sealing element 60 is a silicone seal ring.

In some embodiments, the conductive element 40 and the sealing element 60 of the connector assembly shown in the figure are spaced apart from each other.

A manufacturing method of a connector assembly according to the present disclosure is described below in conjunction with the drawings. A general process of manufacturing the connector assembly 100 shown in FIGS. 2 to 6 is described below.

First, the first insulating housing 10 and the second insulating housing 20 having mounting sides are provided, respectively. In some embodiments, the first insulating housing 10 and the second insulating housing 20 are provided by molding. In other embodiments, the first insulating housing 10 and the second insulating housing 20 are provided by additive manufacturing technology or 3D printing technology. The first insulating housing 10 formed in the preceding manner has a first mounting side, the second insulating housing 20 formed in the preceding manner has a second mounting side, and the second mounting side of the second insulating housing and the first mounting side of the first insulating housing are sealingly connected to each other so as to form a sealed housing. The sealed housing defines two connecting hole along an axial direction and parallel to each other, a hole wall of each connecting hole defines at least one circumferential mounting groove, and the at least one circumferential mounting groove is arranged along the axial direction of the connecting hole. In addition, the first insulating housing 10 and the second insulating housing 20 are further provided with the seal bump 12 and the seal groove 22.

The second mounting side of the second insulating housing and the first mounting side of the first insulating housing are sealingly connected to each other so as to form the sealed housing; and one end of the electrical contact element is extended to an outside of the connector assembly.

Next, multiple conductive elements 40 are respectively arranged in circumferential mounting grooves so that each conductive element 40 is correspondingly connected to one electrical contact element 50. The electrical contact element 50 is connected to the conductive element 40. As mentioned above, each electrical contact element 50 may be connected to each conductive element 40 by soldering or the like, which is not be repeated here.

After that, the seal bump 12 is aligned with and inserted into the seal groove 22 so that the first insulating housing 10 and the second insulating housing 20 are connected to each other at the mounting sides, and the mounting sides of the first insulating housing 10 and the second insulating housing 10 clamp the sheet-like electrical contact element 50. Therefore, an end of the sheet-like electrical contact element 50 is external to the connector assembly 100.

It is to be noted that, in addition to being fixedly connected by the seal bump 12 and the seal groove 22, the first insulating housing 10 and the second insulating housing 20 may also be connected to each other by other fixing manners mentioned above (for example, a sealing strip, adhesives, ultrasonic welding sealing, and the like).

In some embodiments, the step of connecting the electrical contact element 50 to the conductive element 40 may be omitted. In an embodiment, the conductive element 40 and the electrical contact element 50 may be integrally formed, thereby greatly saving processing time and improving processing accuracy. In an embodiment, the conductive element 40 may be an annular coil spring, and the electrical contact element 50 is a contact lead directly formed by extending a spring wire of the conductive element 40 which is the annular coil spring. In a process of producing the connector assembly, the annular coil spring may be directly arranged in the circumferential mounting groove, and the contact lead may be drawn out from the lead hole 26c similar to the lead hole shown in FIG. 9.

In some embodiments, the connector assembly is used in an implantable medical device. The implantable medical device may be deep brain stimulation (DBS), implanted cerebral cortex stimulation (a central nervous system, CNS), implanted spinal cord stimulation (SCS), implanted sacral nerve stimulation (SNS), implanted vagus nerve stimulation (VNS), an implanted cardiac electrical stimulation system (such as a cardiac defibrillator and a cardiac pacemaker), an implantable drug infusion system (IDDS), and the like.

In some embodiments, the implantable medical device includes a sealed housing, electronic circuits and battery elements disposed in the sealed housing, the connector assembly, the externally extending wires, and sensors and/or electrodes disposed outside the sealed housing. The electronic circuits and battery elements disposed in the sealed housing are connected to the electrical contact elements of the connector assembly, and the external electrodes or sensors are connected to the conductive elements of the connector assembly through the connector terminals of the externally extending wires, so as to achieve the electrical connection between the electronic circuits and battery elements in the sealed housing of the implantable medical device and the external sensors or electrodes. A nerve stimulator is used as an example. Through the connector assembly, a pulse generator disposed in a sealed housing transmits pulses generated by the pulse generator to an electrode arranged at a specific position, so as to perform electrical stimulation at that position.

It is to be noted that although several modules or submodules of the connector assembly are mentioned in the preceding detailed description, this division is merely illustrative and not mandatory. In fact, according to embodiments of the present disclosure, features and functions of two or more modules described above may be embodied in one module. Conversely, features and functions of one module described above may be further divided into and embodied by multiple modules.

Other modifications to the disclosed embodiments may be understood and implemented by those of ordinary skill in the art from a study of the specification, the disclosure, the drawings and the appended claims. In the claims, the word "comprising" does not exclude other elements or steps and the words "a" and "an" do not exclude plurals. In a practical application of the present disclosure, one part may perform functions of several technical features referenced in the claims. Any reference numerals in the claims shall not be construed as a limitation to the scope.

What is claimed is:

1. A connector assembly for use in an implantable medical device, comprising:
    an insulating sealed housing, wherein the sealed housing defines at least one connecting hole along an axial direction of the sealed housing, a hole wall of each of the at least one connecting hole defines at least one circumferential mounting groove, and the at least one circumferential mounting groove is arranged along an axial direction of the at least one connecting hole; and
    at least one conductive element, wherein the at least one conductive element is disposed in a corresponding one of the at least one circumferential mounting groove and is drawn out to an outside of the sealed housing through a respective electrical contact element;
    wherein the sealed housing comprises at least:
        a first insulating housing having a first mounting side; and
        a second insulating housing having a second mounting side, wherein the second mounting side of the second insulating housing is sealingly connected to the first mounting side of the first insulating housing to form the sealed housing; and
    wherein the first insulating housing and the second insulating housing are arranged sequentially along a first direction perpendicular to the axial direction of the at least one connecting hole.

2. The connector assembly for use in an implantable medical device of claim 1, wherein the at least one connecting hole is defined by the first insulating housing or the second insulating housing or defined by connection of at least the first insulating housing and the second insulating housing.

3. The connector assembly for use in an implantable medical device of claim 1, wherein the connector assembly further comprises:
    at least one sealing element, wherein the at least one sealing element is respectively disposed in the at least one circumferential mounting groove, and the at least one sealing element and the at least one conductive element are alternately arranged.

4. The connector assembly for use in an implantable medical device of claim 1, wherein the connector assembly further comprises at least one sealing element; and the at least one circumferential mounting groove comprises at least one first mounting groove and at least one second mounting groove, wherein the at least one first mounting groove and the at least one second mounting groove are alternately arranged; and the at least one conductive element is disposed in the at least one first mounting groove, and the at least one sealing element is disposed in the at least one second mounting groove.

5. The connector assembly for use in an implantable medical device of claim 1, wherein each of the at least one conductive element is an annular conductive element.

6. The connector assembly for use in an implantable medical device of claim 5, wherein the annular conductive element is an annular coil spring.

7. The connector assembly for use in an implantable medical device of claim 6, wherein the electrical contact element is a contact lead formed by extending a spring wire of the annular coil spring.

8. The connector assembly for use in an implantable medical device of claim 6, wherein the electrical contact element is a contact lead at least partially abutting against the annular coil spring.

9. The connector assembly for use in an implantable medical device of claim 1, wherein each of the at least one conductive element and a respective electrical contact element are configured to be a single element.

10. The connector assembly for use in an implantable medical device of claim 1, wherein the electrical contact element is a conductive layer disposed on a surface of the at least one circumferential mounting groove, and the conductive layer is drawn out through a through hole to the outside of the sealed housing.

11. The connector assembly for use in an implantable medical device of claim 7, wherein the connector assembly further comprises at least one adapter piece, and the at least one adapter piece is electrically connected to the electrical contact element.

12. The connector assembly for use in an implantable medical device of claim 1, wherein the insulating sealed housing further comprises a fixing through hole, wherein the fixing through hole is communicated with the at least one connecting hole and is used for installing a fixing element to fix a connector terminal inserted into the at least one connecting hole.

13. The connector assembly of claim 1, wherein the sealed housing defines two connecting holes aligned parallel to each other.

14. The connector assembly for use in an implantable medical device of claim 13, wherein the at least one conductive element disposed in the two connecting holes are disposed symmetrically with respect to axes of the two connecting holes.

15. The connector assembly for use in an implantable medical device of claim 1, wherein the first mounting side of the first insulating housing and the second mounting side of the second insulating housing are fixed and sealed directly or fixed and sealed through a seal structure.

16. The connector assembly of claim 15, wherein the seal structure comprises:
    a seal bump extending from an edge of one of the first mounting side or the second mounting side; and
    a seal groove extending from an edge of another one of the first mounting side or the second mounting side;
    wherein the seal bump and the seal groove mate with each other so as to form a fixed and sealed connection between the first insulating housing and the second insulating housing.

17. The connector assembly of claim 15, wherein the seal structure comprises:
    a seal groove disposed on surfaces of mounting sides of the first insulating housing and the second insulating housing;
    a profiled seal ring disposed in the seal groove; and
    a fixing structure disposed on the first insulating housing and the second insulating housing, respectively.

18. An implantable medical device comprising the connector assembly of claim 1.

19. The implantable medical device of claim 18, wherein the implantable medical device is an implantable pulse generator.

20. A manufacturing method of a connector assembly for use in an implantable medical device, wherein the method comprises:
    providing at least a first insulating housing and a second insulating housing, wherein the first insulating housing has a first mounting side, and the second insulating housing has a second mounting side, wherein at least the second mounting side of the second insulating housing is sealingly connected to the first mounting side of the first insulating housing to form a sealed housing; and the sealed housing defines at least one connecting hole along an axial direction of the sealed housing, a hole wall of each of the at least one connecting hole defines at least one circumferential mounting groove, and the at least one circumferential mounting groove is arranged along an axial direction of the at least one connecting hole;

providing at least one conductive element, installing the at least one conductive element in a corresponding one of the at least one circumferential mounting groove, and connecting the at least one conductive element to one electrical contact element;

sealingly connecting the second mounting side of the second insulating housing to the first mounting side of the first insulating housing to form the sealed housing, wherein the first insulating housing and the second insulating housing are arranged sequentially along a first direction perpendicular to the axial direction of the at least one connecting hole; and extending an end of the electrical contact element to an outside of the connector assembly.

21. The connector assembly for use in an implantable medical device of claim 8, wherein the contact lead at least partially abuts against the annular coil spring from at least one of an inside or an outside of the annular coil spring.

22. The connector assembly for use in an implantable medical device of claim 8, wherein the connector assembly further comprises at least one adapter piece, and the at least one adapter piece is electrically connected to the electrical contact element.

23. The connector assembly for use in an implantable medical device of claim 9, wherein the connector assembly further comprises at least one adapter piece, and the at least one adapter piece is electrically connected to the electrical contact element.

24. The connector assembly for use in an implantable medical device of claim 10, wherein the connector assembly further comprises at least one adapter piece, and the at least one adapter piece is electrically connected to the electrical contact element.

25. The connector assembly for use in an implantable medical device of claim 21, wherein the connector assembly further comprises at least one adapter piece, and the at least one adapter piece is electrically connected to the electrical contact element.

26. A connector assembly for use in an implantable medical device, comprising:

an insulating sealed housing, wherein the sealed housing defines at least one connecting hole along an axial direction of the sealed housing, a hole wall of each of the at least one connecting hole defines at least one circumferential mounting groove, and the at least one circumferential mounting groove is arranged along an axial direction of the at least one connecting hole; and at least one conductive element, wherein the at least one conductive element is disposed in a corresponding one of the at least one circumferential mounting groove and is drawn out to an outside of the sealed housing through a respective electrical contact element;

wherein the sealed housing comprises at least:

a first insulating housing having a first mounting side; and a second insulating housing having a second mounting side, wherein the second mounting side of the second insulating housing is sealingly connected to the first mounting side of the first insulating housing to form the sealed housing; and wherein the first mounting side of the first insulating housing and the second mounting side of the second insulating housing are fixed and sealed directly or fixed and sealed through a seal structure.

\* \* \* \* \*